(12) United States Patent
Schmera et al.

(10) Patent No.: US 7,524,460 B1
(45) Date of Patent: Apr. 28, 2009

(54) SYSTEM AND METHOD OF MOLECULE COUNTING USING FLUCTUATION ENHANCED SENSORS

(75) Inventors: Gabor Schmera, San Diego, CA (US); Laszlo B. Kish, College Station, TX (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1156 days.

(21) Appl. No.: 10/789,510

(22) Filed: Feb. 27, 2004

Related U.S. Application Data (63) Continuation-in-part of application No. 10/677,684, filed on Oct. 2, 2003, now Pat. No. 7,286,942.

(60) Provisional application No. 60/475,058, filed on May 30, 2003.

(51) Int. Cl.
| | |
|---|---|
| G01N 7/00 | (2006.01) |
| G01N 33/00 | (2006.01) |
| G01N 29/02 | (2006.01) |
| G01N 25/18 | (2006.01) |

(52) U.S. Cl. ............... 422/83; 422/58; 422/68.1; 73/1.02; 73/19.03; 73/23.2; 73/23.21; 73/23.36; 73/24.01; 436/43; 436/149

(58) Field of Classification Search ............... None
See application file for complete search history.

(56) References Cited

U.S. PATENT DOCUMENTS 4,947,677 A * 8/1990 Frye et al. ............... 73/38

5,571,944 A * 11/1996 Pfeifer et al. ............... 73/24.04

OTHER PUBLICATIONS

Schmera, Kish, Fluctuation-Enchanced Gas Sensing By Surface Acoustic Wave Devices, Fluctuation and Noise Letters, vol. 2, No. 2 (2002) L117-L123 World Scientific Publishing Company.

Kish, Vajtai, Granqvist, Extracting Information from Noise Spectra of Chemical Sensors: Single Sensor Electronic Nose and Tongues, Elsevier sensors and actuators B 71 (2000) 55-59.

(Continued)

*Primary Examiner*—Jill Warden
*Assistant Examiner*—Neil Turk
(74) *Attorney, Agent, or Firm*—Kyle Eppele; Peter A. Lipovsky; J. Eric Anderson (57) ABSTRACT

A System and Method of Molecule Counting Using Fluctuation Enhanced Sensors includes processes for improved chemical analyte detection and quantification through the measurement and generation of an amplitude density histogram of the measured time series of frequency fluctuations in the instantaneous frequency of a chemical sensor arranged to produce an oscillatory output signal when exposed to chemical substances. The system and method may use a chemical sensor, such as a surface acoustic wave (SAW) device. Statistical analysis produces the amplitude density of the frequency fluctuations, which are represented as a pattern that includes information about the quantity of the analyte on the surface of the sensor. Patterns in the measured amplitude density are then correlated to theoretical amplitude density functions in order to determine the number of analyte molecules on the surface of the sensor.

4 Claims, 6 Drawing Sheets

OTHER PUBLICATIONS

Bryant, Poirier, Lee, Vetelino. A Surface Acoustic Wave Gas Detector, 36th Annual Frequency Control Symposium—1982 p. 276-283.

Watson, Staples. Saw Resonators as Vapor Sensors, Amerasia Technology, Inc., Westlake Village Ca 91361 (1990) Ultrasonics Symposum p. 311-314.

Vig, Kim, Noise in Microelectromechanical System Resonators, IEEE Transactions on Ultrasonics, Ferroelectrics, and Frequency Control, vol. 46, No 6 (Nov. 1999) p. 1558-1565.

Schmera, Bulsara, Pierson, Moss Di Cera. Looking at Fokker-Planck Dynamics with a Noisy Instrument. Reprinted from Journal of Statistical Physics vol. 71, No. 5/6 (Jun. 1993) p. 1179-1190.

* cited by examiner

FIG. 6

SYSTEM AND METHOD OF MOLECULE COUNTING USING FLUCTUATION ENHANCED SENSORS

CROSS-REFERENCE TO RELATED APPLICATIONS

This application is a continuation-in-part of commonly-assigned, Non-Provisional application Ser. No. 10/677,684, entitled System and Method of Fluctuation Enhanced Gas-Sensing using SAW devices, filed Oct. 2, 2003 now U.S. Pat. No. 7,286,942, herein incorporated by reference. Application Ser. No. 10/677,684 claims the benefit of Provisional Application No. 60/475,058, filed May 30, 2003, also, herein incorporated by reference.

FEDERALLY-SPONSORED RESEARCH AND DEVELOPMENT

The SYSTEM AND METHOD OF MOLECULE COUNTING USING FLUCTUATION ENHANCED SENSORS is available for licensing for commercial purposes. Licensing and technical inquiries may be directed to the Office of Patent Counsel, Space and Naval Warfare Systems Center, San Diego, Code 20012, San Diego, Calif., 92152; telephone (619)553-3001, facsimile (619)553-3821.

SUMMARY OF THE INVENTION

In one aspect of the invention, a method for analyzing a chemical analyte includes the steps of: (1) generating a fluctuation output signal in response to a plurality of frequency fluctuations in the oscillatory output signal of a surface acoustic wave (SAW) sensor where the fluctuations are responsive to adsorption of molecules on a surface of the SAW sensor; (2) transforming the fluctuation output signal into an amplitude density signal that represents the amplitude density of the frequency fluctuations; and (3) generating an analyte output signal that is representative of a total number of the adsorbed molecules.

In another aspect of the invention, a chemical sensor system is provided that includes a chemical sensor arranged to produce an oscillatory output signal responsive to adsorption of molecules of a chemical analyte by a primary surface of the sensor. The chemical sensor system also includes: measurement means for measuring a plurality of frequency fluctuations of the oscillatory output signal of the sensor; amplitude density means for generating an amplitude density signal representative of the amplitude density of the frequency fluctuations; and decision means for generating an analyte output signal representative of a total number of the adsorbed molecules in response to the amplitude density signal.

In still another aspect of the invention a computer program product (CPP) is provided that includes a machine-readable recording medium and a first, second, and third instruction means recorded on the medium for use with a chemical sensor system that includes a chemical sensor arranged to produce an oscillatory output signal when exposed to a chemical analyte. The first, second, and third instruction means are recorded on the medium for directing the chemical sensor system to: (1) generate a fluctuation output signal in response to a plurality of frequency fluctuations in the oscillatory output signal of the chemical sensor; (2) generate an amplitude density signal representative of the amplitude density of the frequency fluctuations; and (3) generate an analyte output signal that identifies a total number of adsorbed molecules of the analyte.

In yet another aspect of the invention, a method for analyzing a chemical analyte includes the steps of: (1) generating a surface acoustic wave across a surface of a structure; (2) transducing the surface acoustic wave into an oscillatory output signal; (3) generating a fluctuation output signal in response to a plurality of frequency fluctuations in the oscillatory output signal, where the fluctuations are responsive to the adsorption of molecules of the chemical analyte on the surface of the structure; (4) generating an amplitude density histogram in response to the fluctuation output signal; and (5) generating an analyte output signal that identifies a total number n of the adsorbed molecules.

DESCRIPTION OF SOME EMBODIMENTS

Following is a glossary of terms used to describe the system and method for molecule counting using fluctuation enhanced sensors. The definitions set forth in the glossary are representative of the intended meanings as used herein.

GLOSSARY

The term "amplitude density" $g(U)$ may be mathematically defined as follows: $P(U_o, dU) = g(U) \cdot dU$, where $P(U_o, dU)$ is the probability of finding the amplitude around the amplitude value $U_o$ in the range of dU width. The amplitude density may be approximated by an amplitude density histogram of the measured time series.

The term "bandpass filter" means a wave filter that attenuates frequencies on one or both sides of a single transmission band.

The term "chemical analyte" means a substance being measured in an analytical procedure.

The term "chemical sensor" means a device that responds to chemical stimulus.

The term "diffusion coefficient" means a coefficient used to represent the random motion of the molecules on the surface of the SAW device. By way of example, the diffusion coefficient may be represented by: $\langle r^2 \rangle \propto D \cdot t$, where r is the distance traveled by an analyte molecule, D is the diffusion coefficient, t is elapsed time, and where the angle brackets represent the arithmetic mean operation.

The term "frequency counter" means an instrument in which frequency is measured by counting the number of cycles occurring during an established time interval.

The term "machine-readable recording medium" means a physical material in or on which data may be represented wherein the data can be read by an input unit for storage, processing, or display.

Figure 1:
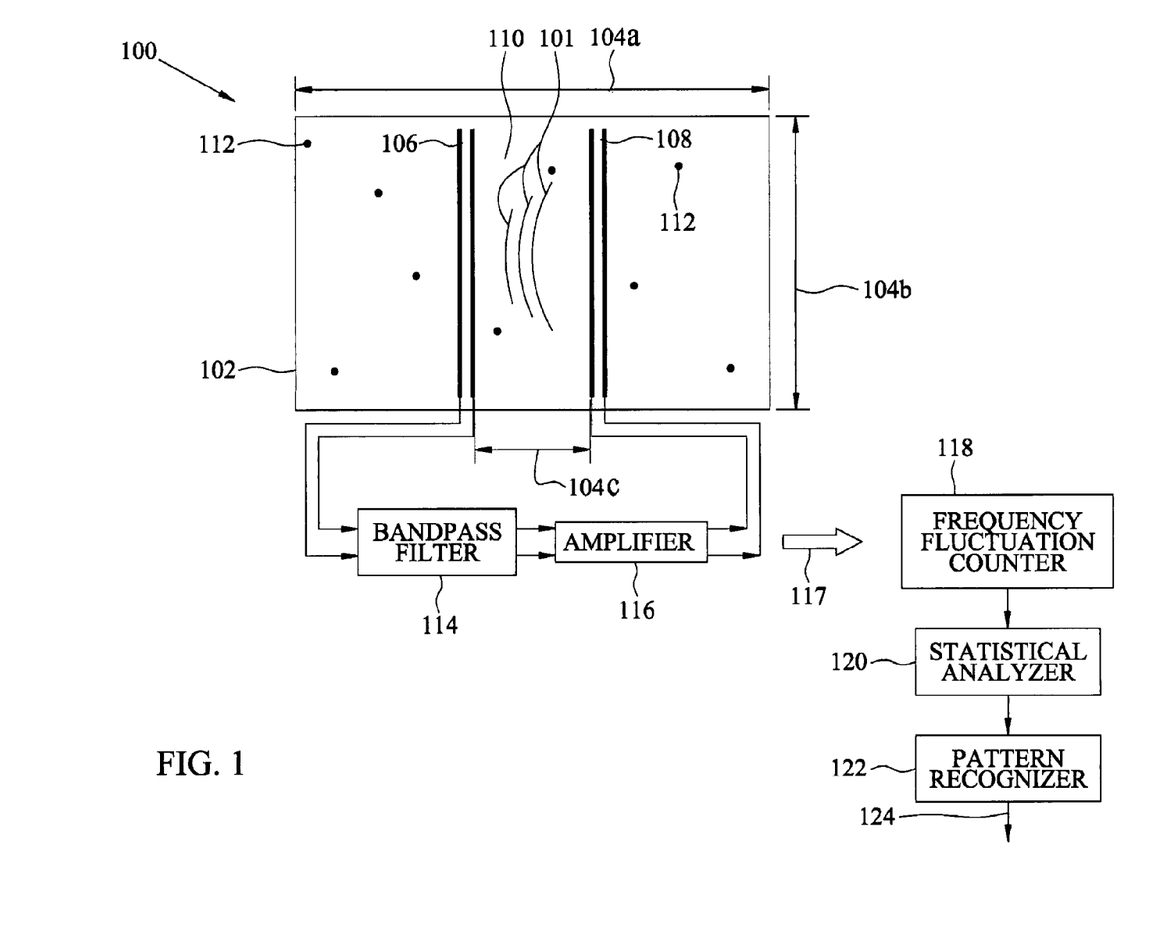
FIG. 1 is a block diagram of a chemical sensor system in accordance with the system and method of molecule counting using fluctuation enhanced sensors.

FIG. 1 shows a block diagram of a gas-sensing SAW device 102 in a chemical sensor system 100, in accordance with the system and method of molecule counting using fluctuation enhanced sensors. SAW device 102 typically includes two electrode pairs 106 and 108. Although SAW device 102 is shown in FIG. 1 as only having two electrodes, it is recognized that any number of electrode pairs for the generation and measurement of surface propagating waves on a SAW device may be implemented. The space between electrode pairs 106 and 108 is referred to as the gas-sensing region 110 or the "sweetspot". In operation, the extra inertial mass of adsorbed molecules 112 decreases the propagation velocity of a generated surface acoustic wave 101 and thus the delay time increases between electrode pairs 106 and 108. The propagation velocity of surface acoustic wave 101 is inversely proportional to the number of adsorbed molecules 112 in the gas-sensing region 110. As used herein, the term gas-sensing zone and active zone are used interchangeably.

Figure 2:
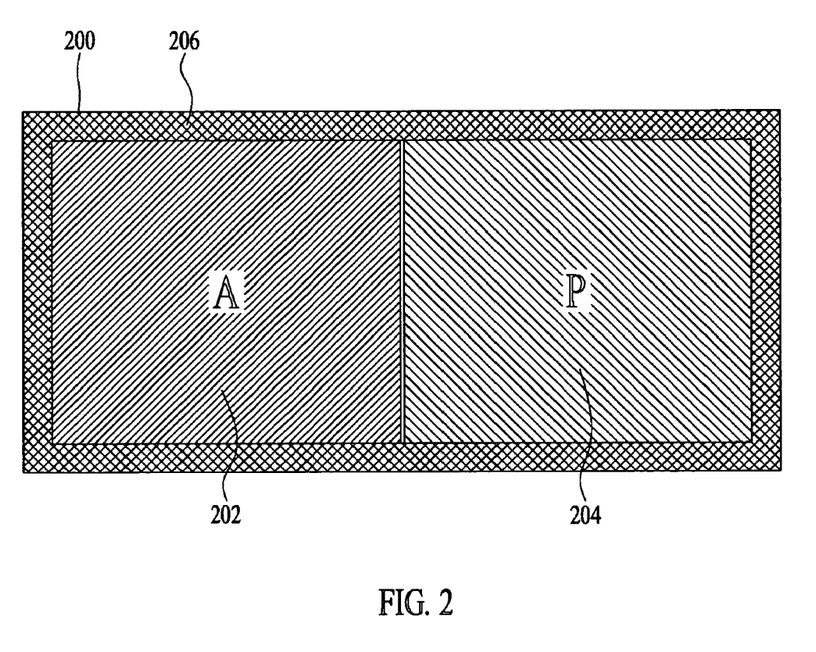
FIG. 2 is a block diagram of a surface of a chemical sensor in accordance with the system and method of molecule counting using fluctuation enhanced sensors.

The gas molecules 112 adsorbed on the surface of SAW device 102 execute a surface diffusion process, which is essentially a random walk over the entire surface of SAW device 102. Assuming that SAW device 102 has a thin and substantially uniform coating over the whole surface, the diffusion coefficient D of the adsorbed gas molecules is constant along the entire surface of SAW device 102. Alternatively, the surface of SAW device 102 may include one or more active zones. FIG. 2 shows an alternative surface 200 of SAW device 102. Asymmetric surface 200 includes active zone 202 and passive zone 204. Also included on asymmetric surface 200 is diffusion barrier 206 that restricts diffusion to zones 202 and 204.

Due to independent random walking of each molecule across the surface of SAW device 102, the instantaneous number N(t) of molecules over gas-sensing region 110 will fluctuate with respect to time. Therefore, chemical sensor system 100 will have fluctuations of the mean oscillation frequency $f_{osc}$ and the instantaneous value $\Delta f_{osc}(t)$ of the frequency deviation from the frequency of the gas-molecule-free case will be proportional to N(t). The dynamical properties of the fluctuations in N(t) and the induced frequency fluctuations $\Delta f_{osc}(t)$ will be determined by the value of D, the geometry of SAW device 102, the gas-sensing region 110, and the active and passive zones.

SAW device 102, in FIG. 1, is not drawn to scale and is shown as having a total length 104a, total width 104b, and gas-sensing region length 104c. The primary surface of SAW device 102 has an area defined by total length 104a and total width 104b. By way of example, SAW device 102 may detect one type of molecule with a characteristic diffusion time constant $\tau_L$ that is much shorter than a characteristic adsorption-desorption time constant $\tau_{ad}$. The characteristic diffusion time $\tau_L$ may be defined as $$\tau_L = \frac{L^2}{D},$$

where L is the total length 104a of SAW device 102 and D is the diffusion coefficient of the adsorbed gas molecules 112. The characteristic adsorption-desorption time constant $\tau_{ad}$ may be defined as $$\tau_{ad} = \frac{\tau_a \cdot \tau_d}{\tau_a + \tau_d},$$

where $\tau_a$ is the adsorption time constant and $\tau_d$ is the desorption time constant.

The probability of a molecule residing in a zone on the surface of SAW device 102 is substantially proportional to the area of the zone in question. The probability density of the molecule distribution is approximately:

$$P(r, n) = \frac{n!}{r!(n-r)!} \cdot p^r \cdot (1-p)^{n-r}, \quad \text{EQ. 1}$$

where n and r are nonnegative integers, $r \leq n$, n represents the total number of molecules on the surface of SAW device 102, r represents the number of molecules on an active zone, and p is represented by:

$$p = \frac{\mu_{active}}{\mu_{total}},$$

where $\mu_{total}$ is the total area of the surface of the SAW device 102 and $\mu_{active}$ is the area of the active zone.

Chemical sensor system 100 optionally includes a bandpass filter 114, for selecting an oscillatory mode of operation, and amplifier 116 coupled to electrodes 106 and 108.

Also included in chemical sensor system 100 is measurement means for measuring a plurality of frequency fluctuations in oscillatory output signal 117. FIG. 1 shows an example of measurement means as frequency fluctuation counter 118. There are various ways that frequency fluctuation counter 118 may measure these frequency fluctuations. One such method is heterodyning, that is, nonlinearly mixing the oscillatory output signal with a noiseless oscillator signal with a frequency close to the fluctuating signal frequency. At the output of this mixing, the difference of the two frequencies is identified and the relative fluctuations will increase. Zero crossings may then be counted using short-term measurements. The zero crossing measurements would give the actual frequency, while the mean of these would result in the mean frequency. The frequency fluctuations, using this heterodyning method, are the difference of the actual and the mean frequencies.

In the case of an asymmetric surface design, as shown in FIG. 2, the instantaneous amplitude, which is output by frequency counter 118, is: $U_{as}(t) = K \cdot N_A(t)$, where K is a calibration constant and $N_A(t)$ is the instantaneous number of molecules in the active zone.

Chemical sensor system 100 also includes amplitude density means for generating an amplitude density signal that is representative of the amplitude density of the frequency fluctuations measured in frequency fluctuation counter 118. FIG. 1 shows and example of amplitude density means as statistical analyzer 120. Statistical analyzer 120 may generate the amplitude density signal by way of generating an amplitude density histogram of the measured time series output by frequency fluctuation counter 118. By way of example, FIG. 6 (a), (b), or (c) may represent outputs of statistical analyzer 120.

A decision means for generating an analyte output signal 124, that is representative of a total number n adsorbed molecules of the analyte 112, is also included in chemical sensor system 100. Alternatively, analyte output signal may represent a total number of molecules of the analyte 112 in a designated volume. FIG. 1 shows an example of decision means as pattern recognizer 122. Pattern recognizer correlates patterns in the measured amplitude density signal to a theoretical amplitude density histogram generated with EQ. 1. As an example, pattern recognizer 122 may utilize a look-up table, a neural network, or other processing means.

Figure 3:
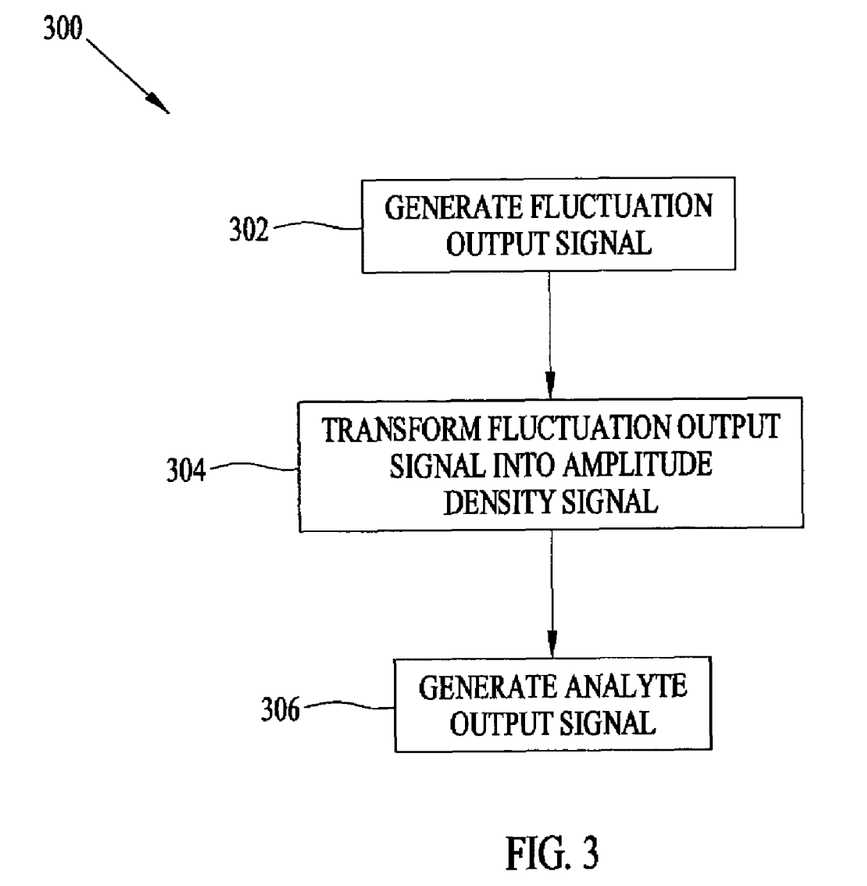
FIG. 3 is a flow-chart of a method in accordance with the system and method of molecule counting using fluctuation enhanced sensors.

FIG. 3 illustrates a method 300 in accordance with the system and method of molecule counting using fluctuation enhanced sensors. Method 300 utilizes statistical analysis of the dynamics of measured frequency fluctuations of a surface acoustic wave (SAW) device that is arranged to produce an oscillatory output signal when exposed to a chemical analyte. Step 302 includes generating a fluctuation output signal in response to a plurality of frequency fluctuations $\Delta f_{osc}$ of the oscillatory output signal. There are various methods that may be implemented for the measurement of the frequency fluctuations. One such method is heterodyning, that is nonlinearly mixing the oscillatory output signal with a noiseless oscillator signal with a frequency close to the fluctuating signal frequency. At the output of this mixing, the difference of the two frequencies is identified and the relative fluctuations will increase. Zero crossings may then be counted using short-term measurements. The zero crossing measurements would give the actual frequency, while the mean of these would result in the mean frequency. The frequency fluctuations, using this heterodyning method, are the difference of the actual and the mean frequencies.

Step 304 transforms the fluctuation output signal into an amplitude density signal that is representative of the amplitude density. The amplitude density may be described, theoretically, by EQ. 1.

Using the measured amplitude density implies strongly enhanced selectivity and sensitivity. One factor contributing to higher sensitivity is the fact that, due to the particular shape of the amplitude density of diffusion processes, the diffusion noise can be easily distinguished from other sensor noise processes, such as adsorption-desorption and thermal noise.

The strongly enhanced selectivity also stems from the fact that the amplitude density is a pattern, not a single number. Therefore, the strength and the shape of the amplitude density contains information about the number of gas molecules.

Lastly, step 306 generates an analyte output signal that is representative of a total number n adsorbed molecules of the chemical analyte, if the amplitude density signal corresponds to a theoretical amplitude density function. As an example, the characteristic signal may be generated by way of a pattern recognizer, a look-up table, or other processing means.

Figure 4:
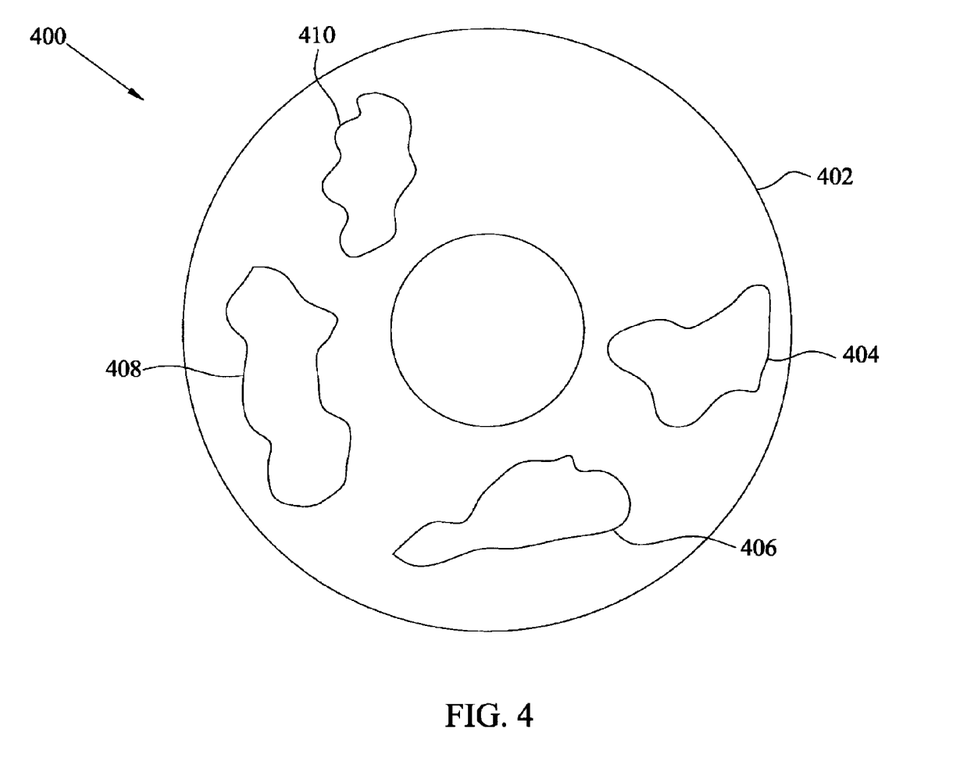
FIG. 4 is a computer program product in accordance with the system and method of molecule counting using fluctuation enhanced sensors.

FIG. 4 illustrates a computer program product (CPP) 400, in accordance with the system and method of molecule counting using fluctuation enhanced sensors. CPP 400 is for use with a chemical sensor system that includes a chemical sensor arranged to produce an oscillatory output signal when exposed to a chemical analyte. CPP 400 includes a machine-readable recording medium 402 and a first, second, and third instruction means, recorded on the recording medium 402.

First instruction means 404 are for directing the chemical sensor system to generate a fluctuation output signal in response to a plurality of frequency fluctuations in the oscillatory output signal generated by the chemical sensor. There are various ways that first instruction means 404 may direct the chemical sensor system to measure these frequency fluctuations. One such method is heterodyning, that is nonlinearly mixing the oscillatory output signal with a noiseless oscillator signal with a frequency close to the fluctuating signal frequency. At the output of this mixing, the difference of the two frequencies is identified and the relative fluctuations will increase. Zero crossings may then be counted using short-term measurements. The zero crossing measurements would give the actual frequency, while the mean of these would result in the mean frequency. The frequency fluctuations, using this heterodyning method, are the difference of the actual and the mean frequencies.

Second instruction means 406 are for directing the chemical sensor system to generate an amplitude density signal that is representative of the amplitude density of the frequency fluctuations in the oscillatory output signal. By way of example, second instruction means 406 may direct the chemical sensor system to generate the amplitude density signal through generation of an amplitude density histogram of the measured time series of frequency fluctuations in the instantaneous frequency.

Third instruction means 408 are for directing the chemical sensor system to generate an analyte output signal that identifies a total number n molecules of the chemical analyte, if the amplitude density signal corresponds to a theoretical amplitude density function. By way of example, the total number of n molecules may represent the total number of molecules on the surface of the chemical sensor. Alternatively, analyte output signal may represent the total number of molecules in a volume. Also, as an example, third instruction means 408 may utilize a look-up table, a neural network, or other processing means.

Optionally included in CPP 400 is a fourth instruction means, recorded on the recording medium 402 for directing the chemical sensor system to correlate patterns in the amplitude density signal to the theoretical density function, as generated by EQ. 1.

Figure 5:
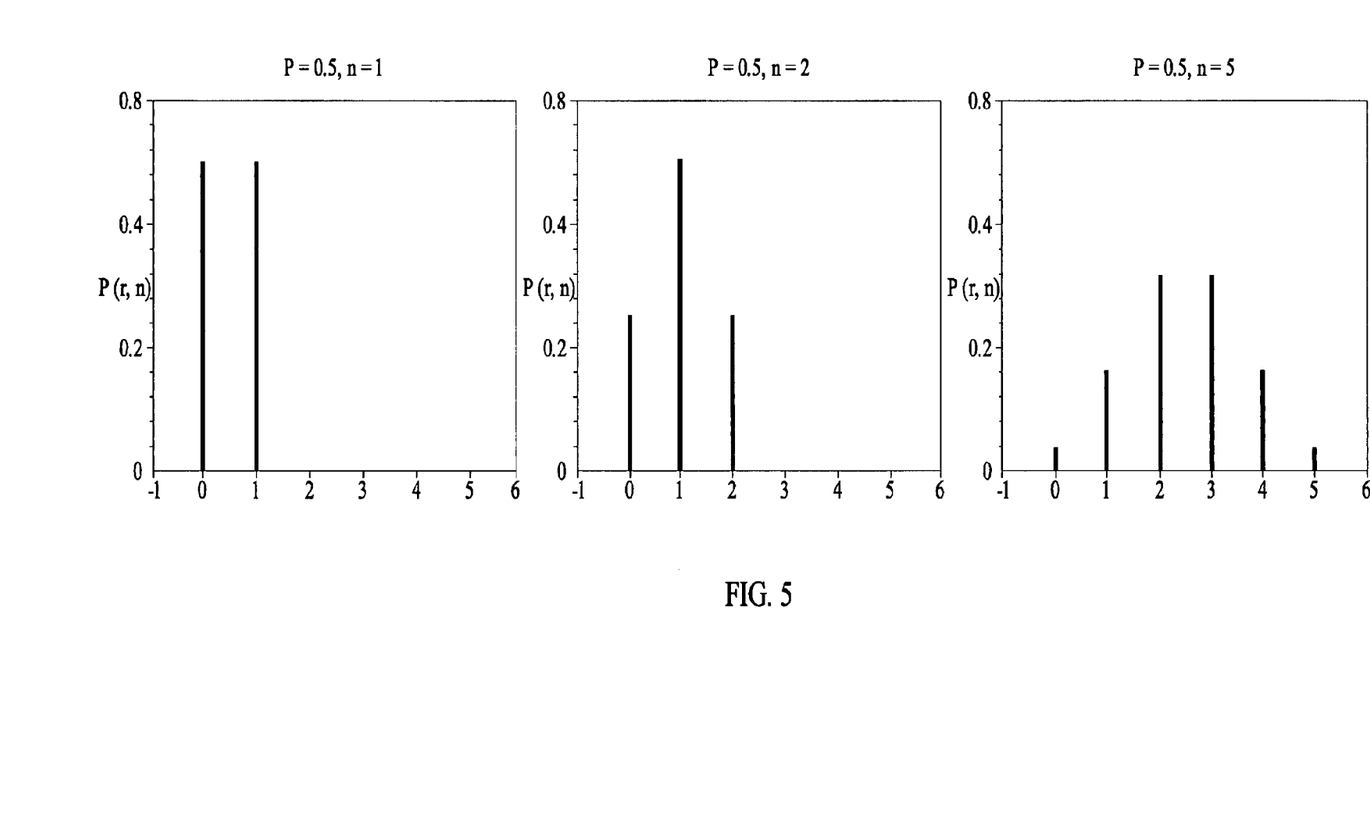
FIG. 5 is a view showing theoretical amplitude density histograms in accordance with the system and method of molecule counting using fluctuation enhanced sensors.

FIG. 5 illustrates theoretical amplitude density histograms in accordance with the system and method of molecule counting using fluctuation enhanced sensors. The three histograms shown were all generated utilizing EQ.1, where p=0.5, and n=1, 2, and 5, respectively.

Figure 6:
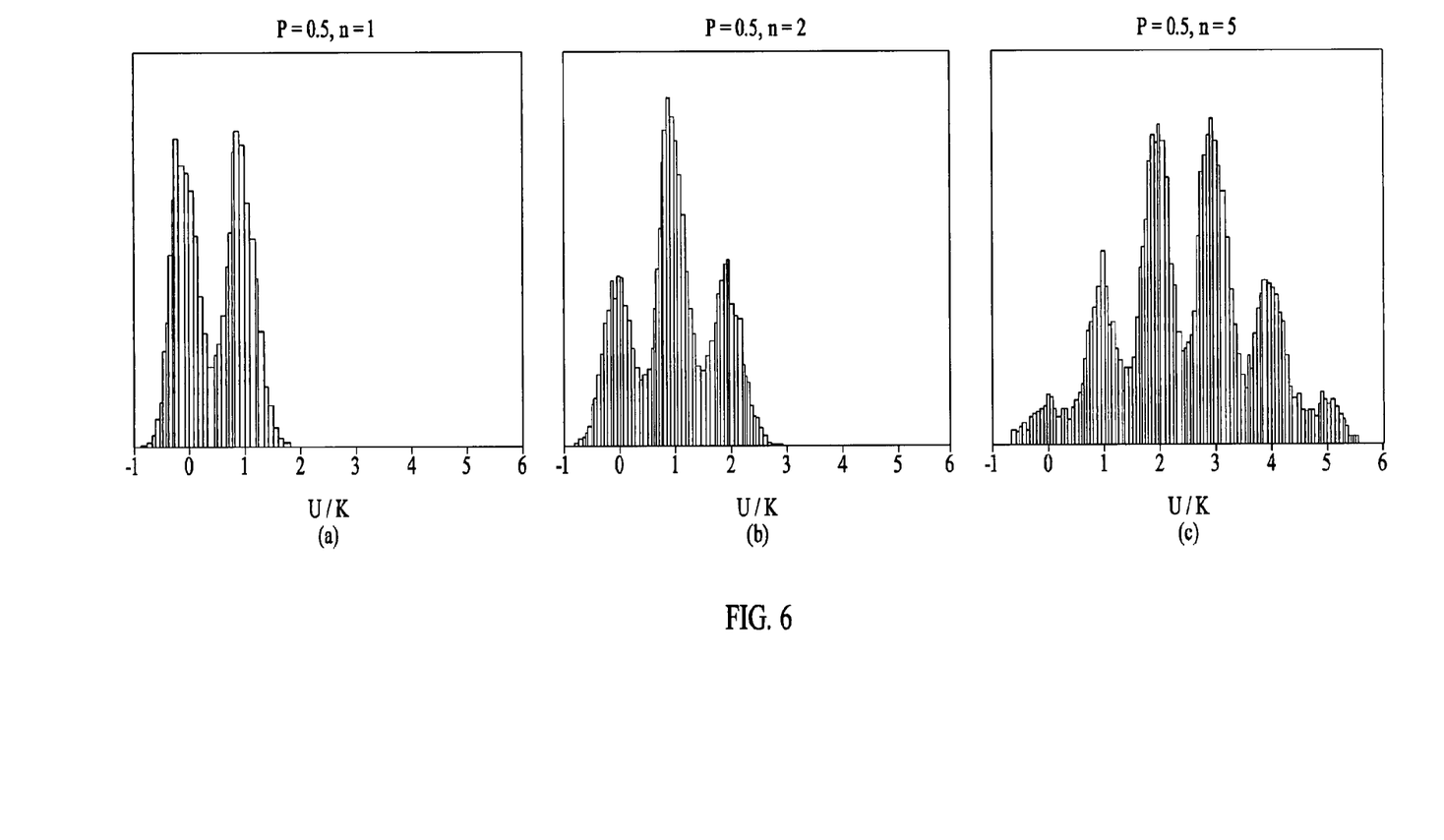
FIG. 6 is a view showing simulated measurements of amplitude density functions in accordance with the system and method of molecule counting using fluctuation enhanced sensors.

FIG. 6 illustrates simulated measurements of the amplitude density functions in accordance with the system and method of molecule counting using fluctuation enhanced sensors. By way of example, FIG. 6 may show outputs of the statistical analyzer 120, of FIG. 1. These measured amplitude densities could then be compared to the theoretical amplitude density histograms, as shown in FIG. 5, to determine the total number of molecules on the surface of the SAW device.

What is claimed is:

1. A chemical sensor system comprising:
   a surface acoustic wave (SAW) sensor comprising a primary surface having a total area and an active zone within the total area, and wherein the SAW sensor is configured to produce an oscillatory output signal responsive to adsorption of molecules of a chemical analyte by the active zone on the primary surface;
   a frequency fluctuation counter configured to measure a plurality of frequency fluctuations of said oscillatory output signal;
   amplitude density means, coupled to said frequency fluctuation counter, for generating an amplitude density signal representative of the amplitude density of said plurality of frequency fluctuations; and
   a pattern recognizer configured to receive the amplitude density signal, wherein the pattern recognizer is also configured to generate an analyte output signal representative of a total number n of said adsorbed molecules if said amplitude density signal corresponds to a theoretical amplitude density function P(r,n) which is substantially represented by the equation:

$$P(r, n) = \frac{n!}{r!(n-r)!} \cdot p^r \cdot (1-p)^{n-r},$$

wherein n and r are nonnegative integers, r≦n, n represents a theoretical total number of molecules on a surface of a virtual SAW sensor, r represents a theoretical number of molecules on an active zone of said virtual SAW sensor, and wherein p is substantially represented by: $p = \mu_{active}/\mu_{total}$, where $\mu_{total}$ is the total surface area of said surface and $\mu_{active}$ is the area of said active zone, wherein said active zone is used to measure an output signal and wherein said total area of said surface is the total area of said SAW device over which an acoustic wave is generated.

2. The chemical sensor system as in claim 1, wherein said primary surface comprises a diffusion barrier that restricts diffusion of said chemical analyte to said primary surface.

3. The chemical sensor system as in claim 1, wherein said chemical sensor further comprises a bandpass filter for selecting a single oscillatory mode.

4. The chemical sensor system as in claim 1, wherein said amplitude density means comprises means for generating an amplitude density histogram of a measured time series of an output of said frequency fluctuation counter.

* * * * *